US008653004B2

(12) United States Patent
Terrenoire et al.

(10) Patent No.: US 8,653,004 B2
(45) Date of Patent: Feb. 18, 2014

(54) ACTIVES-COMPRISING POLYMER NETWORKS, PROCESSES FOR PRODUCING THEM, AND THEIR USE

(75) Inventors: Alexandre Terrenoire, Mannheim (DE); Hartmut Leininger, Neustadt (DE); James Bullock, Grantham (GB); Mohammed Shoaib Qureshi, Bingham (GB); Hans-Werner Schmidt, Bayreuth (DE); Reiner Giesa, Bayreuth (DE); Meik Ranft, Bensheim-Hochstädten (DE); Oscar Lafuente Cerda, Mannheim (DE)

(73) Assignee: BASF SE (DE)

( * ) Notice: Subject to any disclaimer, the term of this patent is extended or adjusted under 35 U.S.C. 154(b) by 651 days.

(21) Appl. No.: 12/671,613

(22) PCT Filed: Jul. 25, 2008

(86) PCT No.: PCT/EP2008/059780
§ 371 (c)(1),
(2), (4) Date: Feb. 1, 2010

(87) PCT Pub. No.: WO2009/016112
PCT Pub. Date: Feb. 5, 2009

(65) Prior Publication Data
US 2012/0157316 A1 Jun. 21, 2012

(30) Foreign Application Priority Data
Aug. 2, 2007 (EP) ..................... 07113711

(51) Int. Cl.
A01N 25/10 (2006.01)
A01N 25/00 (2006.01)
A61K 9/14 (2006.01)

(52) U.S. Cl.
USPC ......... 504/361; 504/116.1; 424/405; 424/487

(58) Field of Classification Search
USPC ......................... 504/361; 424/405
See application file for complete search history.

(56) References Cited

U.S. PATENT DOCUMENTS

| 3,220,960 A | | 11/1965 | Wichterle et al. | |
| 4,177,056 A | | 12/1979 | Mueller et al. | |
| 4,483,759 A | | 11/1984 | Szycher et al. | |
| 5,006,340 A | * | 4/1991 | Atsuta et al. | ............ 514/27 |
| 2002/0151650 A1 | * | 10/2002 | Pathak et al. | ............ 525/90 |

FOREIGN PATENT DOCUMENTS

| DE | 2528068 A1 | 1/1976 |
| DE | 10259673 A1 | 7/2004 |
| DE | 10259674 A1 | 7/2004 |
| EP | 046535 A2 | 3/1982 |
| EP | 0126341 A2 | 11/1984 |
| EP | 212681 A2 | 3/1987 |
| EP | 280222 A2 | 8/1988 |
| EP | 336406 A2 | 10/1989 |
| EP | 686621 A1 | 12/1995 |
| EP | 0903363 A1 | 3/1999 |
| EP | 921168 A1 | 6/1999 |
| EP | 1230855 A1 | 8/2002 |
| EP | 1460089 A1 | 9/2004 |
| GB | 1511563 | 5/1978 |
| GB | 1511563 A * | 5/1978 |
| JP | 51-125142 A | 11/1976 |
| JP | 63081112 A | 4/1988 |
| WO | WO-90/02655 A1 | 3/1990 |
| WO | WO-99/17814 A1 | 4/1999 |
| WO | WO-02/24755 A1 | 3/2002 |
| WO | WO-03/054045 A2 | 7/2003 |
| WO | WO-2004/000953 A1 | 12/2003 |

OTHER PUBLICATIONS

Bojar et al, 1995, British Journal of Dermatology, vol. 132, pp. 204-208.*
Ulubelen et al, Jul. 1994, Phytochemistry, vol. 36, pp. 971-974.*
English Translation of International Preliminary Report on Patentability, Application No. PCT/EP2008/059780, mailed Jul. 15, 2010.

* cited by examiner

Primary Examiner — Brian-Yong Kwon
Assistant Examiner — Mark V Stevens
(74) Attorney, Agent, or Firm — Novak Druce Connolly Bove + Quigg LLP

(57) ABSTRACT

Process for producing actives-comprising polymeric networks from oligomers containing (meth)acrylate groups, optionally from further monomers, and from actives, the polymeric networks obtainable by the process, and the use of the networks for various purposes, more particularly for protecting materials or in crop protection.

10 Claims, 1 Drawing Sheet

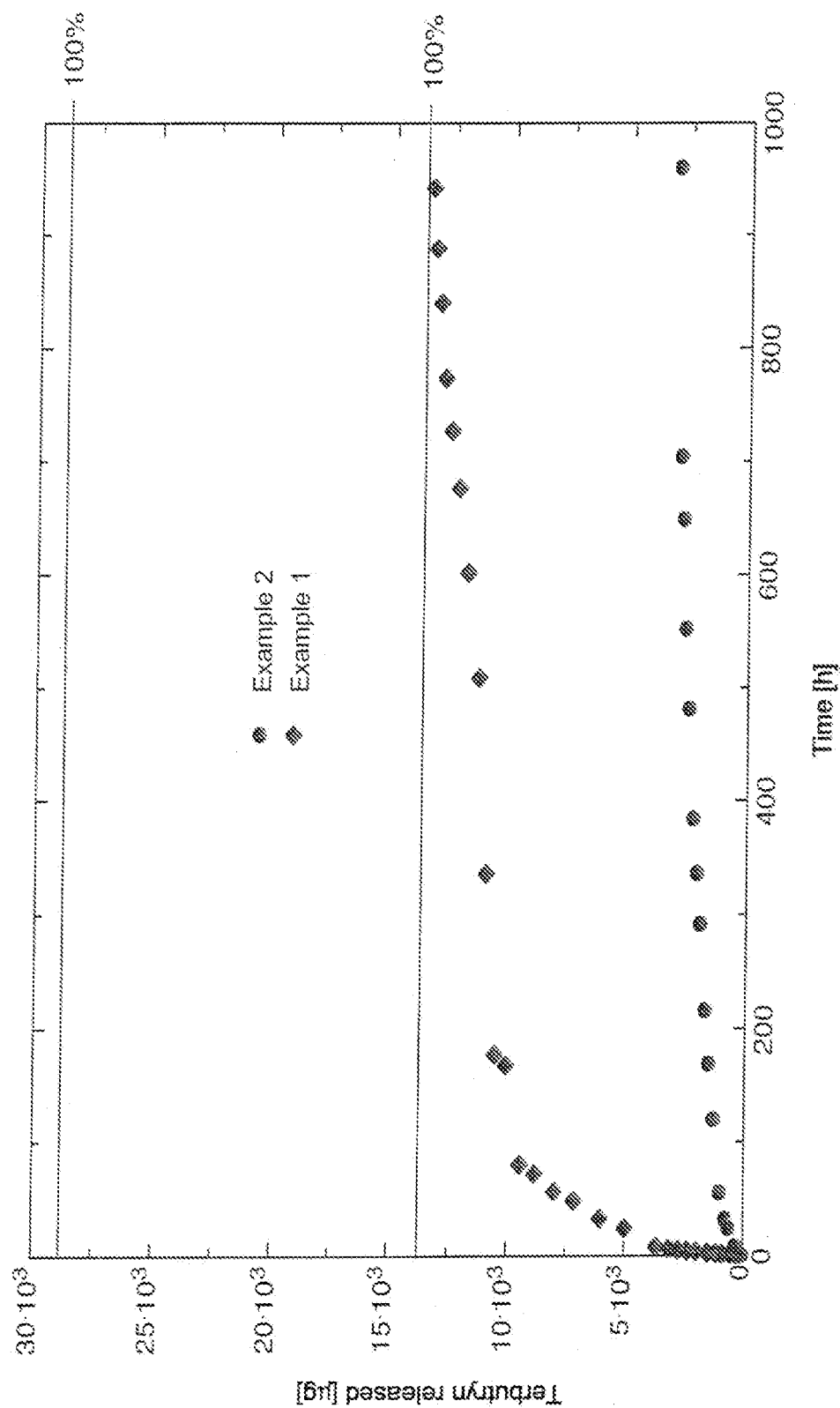

ACTIVES-COMPRISING POLYMER NETWORKS, PROCESSES FOR PRODUCING THEM, AND THEIR USE

CROSS REFERENCE TO RELATED APPLICATIONS

This application is a national phase of PCT/EP2008/059780, filed on Jul. 25, 2008, which claims priority to EP 07113711.1 filed Aug. 2, 2007, the entire contents of all are hereby incorporated by reference.

The invention relates to a process for producing actives-comprising polymeric networks from oligomers containing (meth)acrylate groups, optionally from further monomers, and from actives, the polymeric networks obtainable by the process, and the use of the networks for various purposes, more particularly for protecting materials or in crop protection.

For numerous applications in which actives are used it is desirable for the actives used to be present in the system only at a relatively low concentration, in order to avoid unwanted side-effects, but for this low concentration to be reliably maintained over a relatively long period of time. Examples of this would include biocides which are used as preservatives for paints, films or other materials, and which should always be present in the system only in the minimum effective concentration. For this purpose, systems are needed which effect delayed release of the actives in the system.

In order to delay the release of actives it is known to encapsulate actives. Actives can be enclosed, for example, in microcapsules (core-shell encapsulation), as disclosed for example by WO 90/02655, WO 2004/000953 or EP 1 460 089 A1. With this technique, however, release at a defined rate over a prolonged period of time is not possible, since the active is released immediately the capsule is destroyed.

It is known, furthermore, to incorporate actives into polymeric networks from which the actives are delivered with a delay. This technique is also known as matrix encapsulation.

U.S. Pat. No. 3,220,960 discloses shaped articles comprising hydrophilic copolymers with low degrees of crosslinking and 20% to 97% of water. The principal constituents of the crosslinked copolymers are monoolefinic monomers, specifically (meth)acrylic esters, and also, as a secondary constituent, (meth)acrylic esters which comprise at least two (meth)acrylic acid groups. Dissolved in the water there may be drugs, such as bactericidal substances, for example. The shaped hydrogel articles may be added to the media it is desired to protect.

DE 25 28 068 C2 discloses water-insoluble hydrophilic gels of a copolymer which comprise actives. The copolymers are composed of 10% to 70% by weight of a hydrophobic macromer having a molecular weight of 400 to 8000 g/mol and containing in each case 2 terminal olefinic groups, and of 30% to 90% by weight of a water-soluble monoolefinic monomer, if appropriate also in a mixture with water-insoluble monomers. The actives are accommodated in the gel either by dissolving them in the monomer mixture even before the polymerization or allowing the gel to absorb them after it has been produced. The examples describe the time to release of 90% of the active in water as being 30 to 300 h, depending on the nature of the active. For many applications this is too quick.

It was an object of the invention to provide improved polymeric networks with which an even greater delay can be achieved to the release of active. The network architecture here ought to be adapted very simply to the use of different actives and to the desired release rates. Furthermore, the active should not be altered as a result of its incorporation into the network.

Found accordingly has been a process for producing actives-comprising polymeric networks by mixing polymerizable oligomers and actives and also, optionally, further monomers and/or auxiliaries, followed by thermal or photochemical polymerization of the mixture, wherein the polymerizable mixture comprises the following components:

(A) 19.9% to 99.8% by weight of at least one oligomer containing (meth)acrylate groups and having an average molar mass $M_n$ of 350 to 5000 g/mol, selected from the group of epoxy (meth)acrylates, polyester (meth)acrylates, urethane (meth)acrylates or polyether (meth)acrylates, the arithmetic average of the number of (meth)acrylate groups per oligomer molecule being 2.1 to 5, (B) 0% to 49.8% by weight of at least one monomer containing olefinic groups and having a molar mass $M_n$ of less than 350 g/mol, (C) 0.1% to 8% by weight of at least one polymerization initiator which is soluble in the photopolymerizable mixture, (D) 0.1% to 80% by weight of at least one active which is dispersible or soluble in the photopolymerizable mixture, and (E) 0% to 20% by weight of further auxiliaries and/or additives, the amounts being based in each case on the total amount of all the components of the polymerizable mixture, and the amount of all the components used, (A) to (E), being 100%.

Also found have been actives-comprising polymeric networks obtainable by the stated process.

Found, finally, has been the use of the stated actives-comprising polymeric networks for protecting industrial materials, films, paints, and dispersions, and also in crop protection.

Details of the invention now follow:

Oligomer (A)

The polymerizable mixture for constructing the polymeric networks of the invention comprises at least one oligomer (A) containing (meth)acrylate groups.

The oligomers (A) used are at least one selected from the group of epoxy (meth)acrylates, polyester (meth)acrylates, urethane (meth)acrylates or polyether (meth)acrylates. It will be appreciated that mixtures of two or more different oligomers (A) can also be used. Furthermore, oligomers used may also have two or more of the stated structural features. For example, oligomers can be used which contain ether, epoxy, and urethane units. The terms polyester (meth)acrylates and polyether (meth)acrylates hence also each comprise polyester ether (meth)acrylates.

Oligomers of this kind and their mixtures are known in principle to the skilled worker. Processes for preparing such oligomers are disclosed for example in DE 102 59 673 A1, EP 280 222 A2, EP 686 621 A1 or EP 903 363 A1.

Polyether (meth)acrylates can be obtained in a manner known in principle by esterifying alkoxylated polyols with (meth)acrylic acid.

Alkoxylated polyols can be obtained by methods known to the skilled worker, by reacting polyols with alkylene oxides. Possible forms of implementation are found in Houben-Weyl, Methoden der Organischen Chemie, 4$^{th}$ edition, 1979, Thieme Verlag Stuttgart, ed. Heinz Kropf, volume 6/1a, part 1, pages 373 to 385.

The polyols used can be aliphatic, cycloaliphatic or aromatic polyols. Preferably they are linear or branched aliphatic polyols. Generally speaking the polyols have 4 to 50 carbon atoms, preferably 5 to 40, more preferably 6 to 30, and very preferably 8 to 26. Examples of suitable polyols are disclosed in DE 102 59 673 A1, paragraphs [0011] to [0026]. Examples of preferred polyols comprise trimethylolbutane, trimethylolpropane, trimethylolethane, neopentyl glycol or pentaerythritol, particular preference being given to trimethylolethane, trimethylolpropane, and pentaerythritol.

The polyols may be ethoxylated, propoxylated or mixedly ethoxylated and propoxylated; ethoxylated polyols are preferred. The degree of alkoxylation may be set by the skilled worker in accordance with the desired properties of the polymeric networks. The preferred polyol is trimethylolpropane, trimethylolethane or pentaerythritol with one- to 20-fold, more preferably 5- to 20-fold, very preferably 10-20-fold, and more particularly 12-20-fold alkoxylation, the stated degrees of alkoxylation relating, in a known way, to the average degree of alkoxylation in each case.

The esterification of the alkoxylated polyols with (meth) acrylic acid to give polyether (meth)acrylates can be performed in accordance with the methods described in DE 102 59 674 A1, paragraphs [0038] to [0132].

Polyester (meth)acrylates can be obtained by preparing polyesters in a manner known in principle, starting from dicarboxylic acids, such as adipic acid, and from diols, such as 1,4-butanediol, and also alcohols having more than two OH groups, such as trimethylolethane, trimethylolpropane, and pentaerythritol. The (meth)acrylate groups can be obtained advantageously by reacting terminal COOH groups of the polyester with hydroxyalkyl (meth)acrylates, such as hydroxyethyl acrylate, for example.

Epoxy (meth)acrylates can be obtained, in a manner known in principle, by reacting polyepoxides with (meth)acrylic acid. Epoxide compounds which can be used include, for example, glycidyl ethers of aliphatic or aromatic polyols. Products of this kind are available commercially in large numbers. Particularly preferred are polyglycidyl compounds of the bisphenol A, F or B type, their fully hydrogenated derivatives, and glycidyl ethers of polyhydric alcohols, such as of 1,4-butanediol, 1,4-cyclohexanedimethanol, neopentyl glycol, of 1,6-hexanediol, of glycerol, trimethylolpropane, and of pentaerythritol. Very particular preference is given to bisphenol A diglycidyl ether, 1,4-butanediol diglycidyl ether, trimethylolpropane triglycidyl ether, and pentaerythritol tetraglycidyl ether, more particularly bisphenol A diglycidyl ether. Details of such a reaction are described in DE 102 59 674 A1, paragraphs [0133] to [0143].

In a further embodiment of the invention it is possible to use epoxy (meth)acrylates in a mixture with polyether (meth) acrylates. In the course of the above-described esterification of the alkoxylated polyols with (meth)acrylic acid, the (meth) acrylic acid is used preferably in excess. In order to avoid the removal of excess acrylic acid from the reaction mixture, the excess fraction can easily be removed by adding polyepoxides in stoichiometric amounts, to form epoxy (meth)acrylates. As well as the fully esterified alkoxylated polyol and the epoxy ester, such mixtures may also comprise further products as secondary constituents, such as unesterified or partly esterified alkoxylated polyol and the reaction products thereof with epoxides.

Urethane (meth)acrylates contain both urethane groups and (meth)acrylate groups. They can be obtained, in a manner known in principle, by reacting compounds containing two or more OH groups with diisocyanates or polyisocyanates and also, furthermore, with at least one hydroxyalkyl (meth)acrylate. Suitable diisocyanates or polyisocyanates include, for example, aliphatic, aromatic, and cycloaliphatic diisocyanates and polyisocyanates having an NCO functionality of at least 1.8, preferably 1.8 to 5, and more preferably 2 to 4, and also their isocyanurates, biurets, allophanates, and uretdiones. Preference is given to 2,4- or 2,6-tolylene diisocyanate and the isomer mixtures thereof, hexamethylene diisocyanate, 1,3-bis(isocyanatomethyl)cyclohexane, isophorone diisocyanate, and di(isocyanatocyclohexyl)methane. Hydroxyalkyl (meth)acrylates which can be used with preference include 2-hydroxyethyl (meth)acrylate, 2- or 3-hydroxypropyl (meth)acrylate, 1,4-butanediol mono(meth) acrylate, neopentyl glycol mono(meth)acrylate, glycerol mono(meth)acrylate and di(meth)acrylate, trimethylolpropane mono(meth)acrylate and di(meth)acrylate, and pentaerythritol mono(meth)acrylate, di(meth)acrylate, and tri (meth)acrylate. 2-Hydroxyethyl (meth)acrylate is particularly preferred.

As compounds containing OH groups the abovementioned polyesters can be used. In one particularly preferred embodiment of the invention it is also possible to use the abovementioned mixtures of epoxy (meth)acrylates and polyether (meth)acrylates. Following the esterification with (meth) acrylic acid, the epoxy (meth)acrylates have OH groups which are able to react with isocyanate groups, and incompletely esterified alkoxylated polyols present in the mixture have OH groups. Isocyanate groups remaining after the reaction with diisocyanates and polyisocyanates and also with hydroxyalkyl (meth)acrylates can be deactivated by reaction with monoalcohols such as methanol or ethanol, for example. Further details relating to the preparation of urethane (meth) acrylates are described by DE 102 59 674 A1 in paragraphs [0145] to [0171].

The oligomers (A) have an average molar mass $M_n$ of 350 to 5000 g/mol. Preferably $M_n$ is 400 to 3000 g/mol, more preferably 500 to 2000 g/mol, and very preferably 600 to 1500 g/mol.

The arithmetic average of the number of (meth)acrylate groups per oligomer molecule (A) is 2.1 to 5. By this is meant the average over all of the oligomer molecules that are present in the polymerizable mixture. The average is preferably 2.5 to 4.5 and more preferably 2.8 to 4.2. Consequently there may indeed also be difunctional or monofunctional oligomers present in the mixture, provided the average is maintained.

From among the oligomers (A) that are possible in principle, the skilled worker will make an appropriate selection in accordance with the desired properties of the polymeric network.

The amount of all of the oligomers (A) used together in the polymerizable mixture is 19.9% to 99.8% by weight, preferably 45% to 98% by weight, more preferably 50% to 96% by weight, and very preferably 55% to 95% by weight.

Monomers (B)

Besides the oligomers (A) it is possible, optionally, to use further monomers (B) containing olefinic groups and having a molar mass of less than 350 g/mol. The molar mass is preferably less than 300 g/mol. Monomers of this kind can be used by the skilled worker in order to exert a desired influence on the properties of the polymeric networks, such as the network density or the network's polarity, for example.

The monomers preferably have 1 to 3 olefinic groups. The olefinic groups are preferably (meth)acrylate groups and/or vinyl ether groups, more preferably (meth)acrylate groups, and very preferably acrylate groups.

Examples of monomers (B) which can be used include $C_1$-$C_{20}$ alkyl (meth)acrylates or vinylaromatics having up to 20 C atoms. Examples include methyl (meth)acrylate, ethyl (meth)acrylate, n-butyl (meth)acrylate, 2-ethylhexyl (meth) acrylate or 4-tert-butylcyclohexyl (meth)acrylate. Examples of suitable vinylaromatic compounds include vinyltoluene, α-butylstyrene, 4-n-butylstyrene, 4-n-decylstyrene or styrene. With comparatively apolar monomers (B) of this kind it is possible to obtain networks of reduced polarity.

In one variant of the invention, monomers can be used which possess further functional groups. Using suitably selected groups it is possible to develop secondary interactions, such as the formation of hydrogen bonds, for example, in a targeted way between the network and the active, and accordingly the rate of release of the active can be controlled. Relatively polar networks can be obtained by monomers (B) which are OH-substituted $C_1$-$C_{20}$ alkyl (meth)acrylates or (meth)acrylates containing polyalkylene oxide units, more particularly polyethylene oxide units. Examples include hydroxyethyl (meth)acrylate, hydroxybutyl (meth)acrylate or polyethylene glycol (meth)acrylate.

Examples of further monomers (B) include the tri(meth) acrylic esters of trimethylolpropane, tetra(meth)acrylic esters of pentaerythritol, and their ethoxylated and/or propoxylated derivatives, and di(meth)acrylic esters of dipropylene glycol, tripropylene glycol, diethylene glycol, 1,2-ethanediol, 1,3- or 1,4-butanediol or 1,6-hexanediol. In addition it is also possible, for example, to use monomers (B) which contain COOH groups.

Examples of preferred monomers (B) comprise 1,4-butanediol diacrylate, 1,6-hexanediol diacrylate, dipropylene glycol diacrylate, tripropylene glycol diacrylate, trimethylolpropane triacrylate, dicyclopentadienyl acrylate, and triethylene glycol divinyl ether.

The amount of all of the monomers (B) used together in the polymerizable mixture is 0% to 49.8% by weight, preferably 5% to 45% by weight, more preferably 10% to 40% by weight, and very preferably 20% to 40% by weight.

As a general rule the amount of the monomers (B)—where present—is also made such that the amount of the monomers (B) is not more than 50% by weight, preferably not more than 45% by weight, based on the total amount of oligomers (A) and monomers (B).

Polymerization Initiator (C)

The polymerizable mixture further comprises at least one polymerization initiator which is soluble in the photopolymerizable mixture. The initiators in question may be both photochemically and thermally activable polymerization initiators, which are selected by the skilled worker in accordance with the desired polymerization technique.

Examples of photoinitiators which can be used include mono- or bisacylphosphine oxides, benzophenones or hydroxyacetophenones, their derivatives, or mixtures of these photoinitiators. Specific examples are given in DE 102 59 673 A1 at paragraph [0179] to [0184]. The photoinitiator is selected by the skilled worker in a known way and in accordance with the nature of the radiation to be used.

Thermal initiators which can be used are in principle the initiators known to the skilled worker, provided their thermal stability is such that they do not undergo premature breakdown. Examples comprise dibenzyl peroxide, tert-butyl peroctoate, tert-butyl peroxyisobutyrate or 2,2'-azobis(isobutyronitrile).

The amount of the polymerization initiators is 0.1% to 8% by weight, based on the amount of all the components of the polymerizable mixture, preferably 1% to 6% by weight, and more preferably 2% to 5% by weight.

Actives (D)

The polymerizable mixture further comprises at least one active (D).

The term "active" is understood by the skilled worker to encompass, typically, substances which give rise to an effect or reaction in an organism. Examples include crop protection agents, drugs, biocides, antiseptics, messenger compounds or fragrances and flavors. The term "active" in the sense of this invention is intended to be used in a more comprehensive sense and to include substances which give rise to any effect or reaction in nonliving systems. Examples of such substances include dyes or labeling compounds.

The active (D) is soluble or at least dispersible in the photopolymerizable mixture, and preferably should be soluble in the mixture. To the skilled worker it is self-evident that the solubility will be dependent on the nature of the photopolymerizable mixture, more particularly on the nature of the oligomers (A) and, optionally, of the monomers (B). An active which has good solubility in one oligomer may have a less good solubility in another oligomer. The solubility must be at least high enough for the particular desired concentration to dissolve in the polymerizable mixture. The skilled worker will make an appropriate selection in respect of the oligomer (A) and of the monomer (B) in accordance with the active.

Furthermore, in the course of the polymerization reaction, the active ought as far as possible not to react with the network to form chemical bonds with the network components, so as not to impair the release of the active. More particularly it ought not itself to comprise any olefinically polymerizable groups.

Although soluble auxiliaries are preferred, it is sufficient for the performance of the invention if the auxiliary (D) can be dispersed in the polymerizable mixture, it being possible for the dispersibility to be enhanced, in a way known in principle, by means of corresponding auxiliaries, more particularly of corresponding surfactants.

The amount of all the actives (D) used together in the polymerizable mixture is 0.1% to 80% by weight, preferably 1% to 30% by weight, more preferably 2% to 10% by weight, and very preferably 3% to 8% by weight.

In one preferred embodiment of the present invention the active is a biocide. The biocides in question here may be any kinds of biocidally acting substances, such as, for example, bactericides, fungicides, herbicides, insecticides, algicides, acaricides, microbicides, molluscicides, nematicides, rodenticides or virucides.

The biocides may be, for example, biocides for in-can or in-container preservation, intended to prevent the molding and/or spoilage of the container, more particularly after first-time opening. Examples of materials for protection include, more particularly, packaged emulsion paints or varnishes.

The biocides may also be biocides for film preservation, intended to prevent the infestation of a coating film with molds, bacteria and/or algae.

Examples of suitable biocides comprise 1,2-benzisothiazolin-3-one, 2-methylisothiazolin-3-one, bronopol, zinc pyrithione, N2-tert-butyl-N4-ethyl-6-methylthio-1,3,5-triazine-2,4-diamine (terbutryn), 3-iodo-2-propynylbutyl carbamate, and isothiazolinone derivatives such as methylisothiazolinone, octylisothiazolinone, dichloroctylisothiazolinone or benzisothiazolinone.

Further examples comprise biocidal actives which can be used in crop protection. Examples comprise fungicides such as fenpropimorph, epoxiconazole or dithianon or herbicides such as dicamba, imazapyr, imazamox, imazapic, metazachlor, saflufenacil or terbutryn.

The compounds may preferably be herbicides, such as N2-tert-butyl-N4-ethyl-6-methylthio-1,3,5-triazine-2,4-diamine (terbutryn), for example.

In a further preferred embodiment of the invention, the actives are messengers or scents, in particular pheromones, in particular pheromones for crop protection applications. An example of a pheromone is (Z)-dodec-9-enyl acetate. They can be used, for example, for aggregation (bark beetle trap) or for disorientation (European grape berry moth).

It will be appreciated that mixtures of different actives can also be used. The skilled worker will make an appropriate selection of actives in accordance with the desired end use.

Auxiliaries and Additives (E)

The polymerizable mixture may further comprise 0% to 20% by weight of further auxiliaries and/or additives (E). In this way it is possible to adapt the properties of the polymeric networks correspondingly, in accordance with the end application.

The auxiliaries and/or additives in question may be, for example, oxidation inhibitors, UV stabilizers, activators, fillers, pigments, dyes, degassing agents, gloss agents, antistatic agents, flame retardants, thickeners, thixotropic agents, flow control assistants, binders, antifoams or surfactants.

UV stabilizers may be, for example, oxanilides, triazines and benzotriazole, and benzophenones. They can be used alone or together with suitable free-radical scavengers, examples being sterically hindered amines such as 2,2,6,6-tetramethylpiperidine. 2,6-di-tert-butylpiperidine or their derivatives, an example being bis(2,2,6,6-tetramethyl-4-piperidyl) sebacate.

The amount of further auxiliaries and/or additives (E) is preferably 0% to 15% by weight, more preferably 0% to 10%, and very preferably 0% to 5% by weight.

Producing the Polymeric Networks

The polymeric networks can be produced preferably by photochemically or thermally activated free-radical polymerization of the polymerization formulations.

For this purpose the components (A), (C), (D), and, optionally, (B) and (E) are first of all mixed with one another. Mixing may take place by means of typical mixing assemblies, as for example by means of simple roll mixers. The polymerization initiator is selected in accordance with the desired polymerization technique. Where polymerization is to take place thermally, it should be ensured that the temperature when mixing remains well below the temperature of the 10 h half-life 10 h-$t_{1/2}$, of the initiator. A T(10 h-$t_{1/2}$) of more than 80° C. has been found appropriate.

In one preferred embodiment of the invention the production takes place photochemically. The polymerizable composition for this purpose is generally processed to a thin film, as for example by knifecoating on a suitable substrate such as glass, for example. There is no restriction on the thickness of the film. It may be a film, for example, with a thickness of up to 5 mm, generally of up to 2 mm. A film thickness of 10 to 500 μm has been found appropriate, preferably 20 to 350 μm, more preferably 30 to 250 μm, and very preferably 50 to 200 μm.

The film may subsequently be irradiated with a suitable radiation source for polymerization. Radiation curing takes place preferably by exposure to UV or UV/VIS radiation. Examples of radiation sources used include high-pressure mercury vapor lamps, lasers, pulsed lamps (flashlight), halogen lamps or excimer emitters. It will be appreciated that two or more radiation sources can also be used for curing, which may also emit each in different wavelength ranges.

Irradiation may if appropriate also be carried out in the absence of oxygen, as under an inert gas atmosphere, for example. Suitable inert gases include more particularly nitrogen, noble gases or carbon dioxide.

After crosslinking, the polymerized film can be removed from the substrate. It can be used as it is, or else it can be comminuted after polymerization, to form chips, for example, or can be ground to powders. Particles obtained may have a diameter, for example, of 5 to 100 μm, preferably 10 to 60 μm, without the invention being restricted thereto. It is also possible to use the polymerized film together with the substrate, or to comminute the film together with the substrate.

The thermal polymerization may take place, in the same way as for the photochemical polymerization, by heating a film to a sufficient temperature, it also being possible for the films for thermal polymerization to be thicker than 500 μm.

In one preferred embodiment of the invention the thermal polymerization is implemented as a suspension polymerization (also called bead polymerization). In this case the polymeric network is obtained in the form of fine polymer particles. The technique of suspension polymerization is known in principle to the skilled worker and is described for example by Houben-Weyl, volume E 20, page 1149. Processes for producing products having a particularly uniform particle size distribution are disclosed by EP 046 535 and WO 02/24755.

In the case of suspension polymerization the polymerizable mixture is first suspended in water by means of a suitable dispersing assembly. In this context it has been found appropriate to add a small amount of a suitable surfactant, such as SDS, to the aqueous phase. Subsequently the suspended particles are polymerized by heating of the mixture as a whole, at 80 to 100° C., for example; in certain circumstances, the heat introduced by the dispersing operation may be enough on its own. The size of the particles can be adjusted through the intensity of the dispersing operation and through the surfactant content. The particles may be spherical, ellipsoidal, elongated, planar or else irregular in shape. Preferred particles have a size of 0.2 to 50 μm. In the case of nonspherical particles, this figure refers in each case to the longest axis.

Properties and Use of the Actives-Comprising Polymeric Networks

The polymeric networks comprising actives (D) can be used by contacting the networks with the systems in which the active is to display its effect. This can be done, for example, by contacting an intact film with the system, or by contacting a comminuted material, such as a powder, for example, with the system.

The actives (D) are tied into the network substantially by means of noncovalent interactions. As a result of the tying of the actives into the network, the actives, on the one hand, are delivered to the system only at a greatly retarded rate. Moreover, the actives in the network are protected from environmental effects, with the consequence that they are degraded not at all or at least with a significant retardation. The networks are not water-soluble, with the consequence that water-soluble actives as well can be fixed in an aqueous environment.

The rate of release of the actives can be controlled by chemical and physical parameters. Chemical and physical parameters for control comprise noncovalent interactions between the active and the network, and also the network density and the swelling of the network. Increasing the network density by using an oligomer (A) and/or monomer (B) having a relatively large number of (meth)acrylate groups (three or more, for example) has the general effect of retarding the release of the active. Naturally, the release is quicker at elevated temperatures than at lower temperatures.

Polymeric networks comprising biocides as their actives can be used, for example, for protecting industrial materials, more particularly for protecting the materials from infestation by microorganisms.

Examples of industrial materials comprise preferably liquid industrial materials, more particularly coating materials, paints, impregnating materials, varnishes, colors or printing inks, such as flexographic inks or ink-jet inks, for example, dispersions, such as acrylate or styrene-acrylate dispersions, for example, and also the formulations of such dispersions for use, for example, as wall paint, surface coating or textile assistant. Further examples comprise polyurethane dispersions and their use, as for example for producing clear varnishes for wood, paper or coatings on plastics. The materials may also be products from the architectural sector, such as mason's plasters.

The industrial materials may preferably be paints and/or dispersions. These may preferably be water-based industrial materials, such as aqueous dispersions or aqueous paints, for example. Preference is further given to films of any coating materials.

The polymeric networks comprising actives may be used, for example, by mixing a powder or particles formed from the networks with the industrial material, more particularly with the paints and/or dispersions. This may take place preferably before or else only after the products have been dispensed into appropriate packaging. In this way the industrial materials are protected even on prolonged storage. Following the application of coating materials, more particularly paints and/or dispersions, the resulting films are protected as well.

The nature of the active, more particularly of the biocide used, is guided here by the nature of the material to be protected, and/or by the environment in which the material is to be used. Thus, for example, coating materials for underwater coatings, and the films applied using them, must be protected particularly well against algal infestation. The skilled worker is aware of the actives especially suitable for the particular end use desired.

Depending on the desired application it is also possible to use two or more different actives in combination. This can be accomplished by using two or more actives when producing the networks.

In one particularly preferred embodiment of the invention a combination of at least two different polymeric networks can be used, the polymeric networks each comprising different actives. In this case each polymeric network can be adapted to the active in such a way that the rate of release of actives is the same in each case. In this way a consistent proportion of both actives in the system is ensured.

In a further-preferred embodiment of the invention the active may be a crop protection agent, such as an insecticide or a herbicide, for example. Polymeric networks of this kind can be used for crop protection.

In one preferred crop protection application the active is a herbicide. For optimum activity, herbicides ought not to penetrate the soil too deeply, but should instead remain in the topmost stratum of the ground. On account of their particle size and water insolubility, the particles of the polymeric networks remain at the surface of the earth, or, at least, their penetration into deeper strata is greatly delayed. This ensures an effective concentration of the active at the surface or in top ground strata.

The networks of the invention provide particularly strong retardation of the release of crop protection actives. Accordingly the networks are especially suitable for long-term applications, by greatly increasing the intervals of time at which the areas to be protected must be retreated. Examples of such applications comprise forestry, the treatment of track beds and rail embankments or the treatment of areas under high-voltage lines.

The networks of the invention are suitable, furthermore, for example as components of antifouling paints or coatings, for the treatment of ships' hulls, for example.

The examples which follow are intended to illustrate the invention in more detail.

Starting Materials Used

Preparation of a Urethane Acrylate (A1)

The urethane acrylate used was the urethane acrylate B1 according to the instructions from DE 102 59 673 A1, page 16. The average molar mass $M_n$ is about 1100 g/mol and the average acrylate functionality is about 3.4.

Preparation of a Polyester Acrylate (A2)

The preparation of the polyester acrylate (A2) was performed according to the Example from EP 686 621 A1, pages 5/6. The average molar mass $M_n$ is about 650 g/mol and the average acrylate functionality is about 4.0.

Preparation of a Polyester Acrylate (A3)

The preparation of the polyester acrylate (A3) was performed according to Example 8 from EP 0126341 A1. The average molar mass $M_n$ is about 1100 g/mol and the average acrylate functionality is about 2.6.

Preparation of a Polyether Acrylate (A4)

Trimethylolpropane was first ethoxylated by typical methods (average degree of ethoxylation about 3.5). The ethoxylated trimethylolpropane obtained was then fully esterified with acrylic acid.

The average molar mass $M_n$ is about 450 g/mol and the average acrylate functionality is about 3.0.

Preparation of an Epoxy Acrylate (A5)

The preparation of the epoxy acrylate (A5) was performed according to Example 1a from EP 921 168 A1. The average molar mass $M_n$ is about 510 g/mol and the average acrylate functionality is about 2.4.

Active

The actives D used were:

D1 Terbutryn (N2-tert-butyl-N4-ethyl-6-methylthio-1,3,5-triazine-2,4-diamine, algicide/herbicide)

D2 Dicamba (3,6-dichloro-2-methoxybenzoic acid, herbicide)

D3 Pheromone

The solubility of terbutryn in the urethane acrylate (A1) is 8% to 10% by weight, in the polyether acrylate (A2) 16% to 18% by weight, and in water about 20 mg/l.

Photoinitiator

The photoinitiator used was 2,2-dimethoxy-1,2-diphenylethan-1-one.

EXAMPLES 1 TO 6

Photochemical Production of the Actives-Comprising Polymeric Networks

The oligomer (A), optionally monomer (B), the photoinitiator (C), and the active (D) and also, optionally, (E) were mixed intensely with one another in the amounts indicated in Table 1 using a roller mixer for 10 to 48 h. Subsequently a film was applied in the thickness indicated in Table 1 to a glass plate by means of a doctor blade (Examples 1 to 3: 200 μm; Example 4: 50 μm) and the film was irradiated twice with UV light having an intensity of 130 W/cm, for about 0.5 s each time.

The coated film was carefully removed from the glass plate. A disk 70 mm in diameter was punched from part of the film. The disk was used for experiments on the release of the active.

TABLE 1

Composition of the experiments conducted; all amounts data in each case in % by weight based on the amount of all the components of the polymerizable composition (TMPTA: trimethylolpropane triacrylate)

| Example No. | Oligomer (A) Type | Amount | Monomer (B) Type | Amount | Ratio A/B | Photoinitiator (C) Amount | Active (D) Type | Amount | Film thickness [μm] |
|---|---|---|---|---|---|---|---|---|---|
| Example 1 | A1 | 91 g | — | — | 100/0 | 4 g | D1 | 5 g | 118 |
| Example 2 | A2 | 91 g | — | — | 100/0 | 4 g | D1 | 5 g | 125 |
| Example 3 | A3 | 36.4 g | TMPTA | 54.6 g | 40/60 | 4 g | D1 | 5 g | 115 |
| Example 4 | A3 | 34.4 g | TMPTA | 51.6 g | 40/60 | 4 g | D1 | 10 g | 40 |
| Example 5 | A5 | 71 g | — | — | 100/0 | 4 g | D2 | 25 g | 233 |
| Example 6 | A2 | 90 g | — | — | 100/0 | 4 g | D3 | 10 g | 135 |

EXAMPLE 7

Processing of the Films to a Powder

The coated film obtained according to Example 4 was first removed from the glass plate, in the course of which it already broke down into a number of smaller pieces. Thereafter the pieces were ground using an ultra-centrifugal mill (ZM 100, Retsch), the rotor of the mill having been cooled with dry ice beforehand. Grinding was carried out twice, using a 500 μm annular screen in the first grind and an 80 μm annular screen in the second grind. Particles with a size of about 5 μm to 100 μm were obtained.

EXAMPLE 8

Production of the Actives-Comprising Polymeric Networks by Means of Suspension Polymerization The suspension polymerization was carried out using the oligomer A4.

A mixture of 17.3 g (86.5% by weight) of the oligomer (A4), 2 g of terbutryn (10% by weight), 0.6 g (3% by weight) of dibenzoyl peroxide, and 0.1 g (0.5% by weight) of 1-octadecanol was stirred in the dark for 48 h until a clear solution was obtained. The mixture was subsequently poured into 200 g of a 0.5% strength solution of $NaHPO_4$ in water and the system was dispersed in water using a dispersing assembly (Ultra-Turrax T 25, IKA Labortechnik) at 9500 rpm, with the further addition of 0.2 g of sodium dodecyl sulfate. The mixture was first heated rapidly to 80° C. and then heated further slowly, until the onset of polymerization, at 88 to 92° C. for 10 min. After the polymerization the product obtained was isolated by filtration, washed, and dried. The resulting powder crumbs were carefully comminuted in a mortar. This gave fine particles with a size of about 50 to 200 nm.

The powders obtained can be added directly to the medium it is desired to protect (a paint dispersion, for example).

Test Results

The release of active in contact with water was measured for each of the networks obtained in Examples 1 to 3 and 5.

For this purpose the film disks obtained above were placed at room temperature into a closable vessel containing 40 ml of fully demineralized water, and the vessel was closed and stored at room temperature for a defined time.

Thereafter the disk was removed and was stored in a further vessel containing 40 ml of fresh water at room temperature for a defined time. These treatment cycles were repeated a number of times.

On each storage in water, active was released. The respective concentration of the active in the water was analyzed by means of HPLC before removal of the disk.

The amounts released are in each case summarized in Table 2.

TABLE 2

| No. | Time [h] | Amount of active released |
|---|---|---|
| Example 1 | 290 | 6.5% |
|  | 1010 | 98% |
| Example 2 | 1133 | 11% |
| Example 3 | 31 | 0.6% |
| Example 5 | 192 | 14% |

The time profile of the release of the actives according to Example 1 and Example 2 is collated in FIG. 1.

The results show that the rate of release can be controlled very effectively by selecting the components for the polymeric network, and that release can be delayed to a very great extent by means of the network architecture. In Example 2 only 11% of the active is released even after more than 1000 h.

The invention claimed is:

1. A process for producing an actives-comprising polymeric network for delayed release of actives, the process comprising:
   forming a polymerizable mixture by mixing
   (A) 19.9% to 99.8% by weight of at least one oligomer containing (meth)acrylate groups and having an average molar mass $M_n$ of 350 to 5000 g/mol, selected from the group consisting of epoxy (meth)acrylates, polyester (meth)acrylates, urethane (meth)acrylates or polyether (meth)acrylates; the arithmetic average of the number of (meth)acrylate groups per oligomer molecule being 2.1 to 5,
   (B) 0% to 49.8% by weight of at least one monomer containing olefinic groups and having a molar mass $M_n$ of less than 350 g/mol,
   (C) 0.1% to 8% by weight of at least one polymerization initiator comprising a thermal polymerization initiator and/or a photochemical polymerization initiator which is soluble in the polymerizable mixture,
   (D) 0.1% to 80% by weight of at least one active selected from the group consisting of biocides, herbicides, messengers, scents and combinations thereof, which is dispersible or soluble in the polymerizable mixture, and
   (E) 0% to 20% by weight of further auxiliaries and/or additives,
   to form the polymerizable mixture, the amounts being based in each case on the total amount of all the components of the polymerizable mixture, and the amount of all the components used, (A) to (E), being 100%; and thermally or photochemically polymerizing the polymerizable mixture.

2. The process according to claim 1, wherein the resulting polymeric networks are processed to a powder after the polymerization.

3. The process according to claim 1, wherein the polymerization is performed photochemically by processing the polymerizable mixture to a film with a thickness of 10 to 500 μm, irradiating the film utilizing actinic radiation and comminuting the film after polymerization.

4. The process according to claim 1, wherein the polymerization is performed thermally utilizing the technique of suspension polymerization, the size of the particles of the polymeric network that are formed in the course of the suspension polymerization being 0.2 to 50 μm.

5. The process according to claim 1, wherein the average molar mass $M_n$ of the oligomers is 400 to 3000 g/mol.

6. The process according to claim 1, wherein the average of the number of (meth)acrylate groups per oligomer molecule is 2.5 to 4.5.

7. The process according to any claim 1, wherein the olefinic monomers (B) are monomers containing (meth)acrylate groups and/or vinyl ether groups.

8. The process according to claim 1, wherein the monomers (B) containing olefinic groups contain 1 to 3 olefinic groups.

9. The process according to claim 1, wherein at least two different actives are used.

10. The process according to claim 2, wherein the average molar mass $M_n$ of the oligomers is 400 to 3000 g/mol.

\* \* \* \* \*